United States Patent [19]

Putsch

[11] 4,112,928

[45] Sep. 12, 1978

[54] ERGOMETER

[75] Inventor: Peter Ulrich Putsch, Rockenhausen, Germany

[73] Assignee: Keiper Trainingsysteme GmbH & Co., Rockenhausen, Germany

[21] Appl. No.: 721,436

[22] Filed: Sep. 8, 1976

[30] Foreign Application Priority Data

Sep. 11, 1975 [DE] Fed. Rep. of Germany ....... 2540493

[51] Int. Cl.² .............................................. A61B 5/02
[52] U.S. Cl. .............................. 128/2.05 R; 128/2.07; 272/73; 272/DIG. 6
[58] Field of Search ..................... 272/69, 73, DIG. 6; 128/2.07, 2.05 R

[56] References Cited

U.S. PATENT DOCUMENTS

| | | | |
|---|---|---|---|
| 3,511,097 | 5/1970 | Corwin | 272/73 |
| 3,675,640 | 7/1972 | Gatts | 128/2.05 R |
| 3,744,480 | 7/1973 | Gause et al. | 272/73 |
| 3,767,195 | 10/1973 | Dimick | 272/73 |
| 3,848,467 | 11/1974 | Flavell | 73/379 |
| 3,940,742 | 2/1976 | Hudspeth et al. | 340/172.5 |
| 3,991,304 | 11/1976 | Hillsman | 128/2.08 |

OTHER PUBLICATIONS

Graf, R. E., "Modern Dictionary of Electronics," Howard Sams & Co., Indianapolis, 1970, pp. 32, 99.

*Primary Examiner*—Robert W. Michell
*Assistant Examiner*—Francis J. Jaworski
*Attorney, Agent, or Firm*—Wigman & Cohen

[57] ABSTRACT

This disclosure relates to an ergometer for measuring physical exercise parameters during the application of physical energy by a user. The ergometer includes an arithmetic computer having a digital display device for determining and indicating various exercise parameters during the expenditure of physical energy by the user. The computer includes a stored program of exercise parameters and an input unit having a keyboard whereby personal data of the user, e.g., age, weight and sex, may be fed into the computer to be taken into account in the determination of physiological values during an exercise program. A heart-pulse receiver adapted to be connected to the user feeds values corresponding to the heart-pulse frequency of the user into the computer.

9 Claims, 4 Drawing Figures

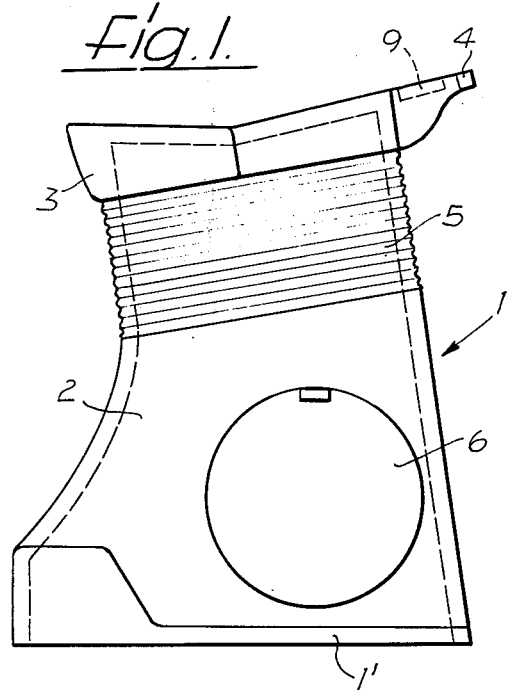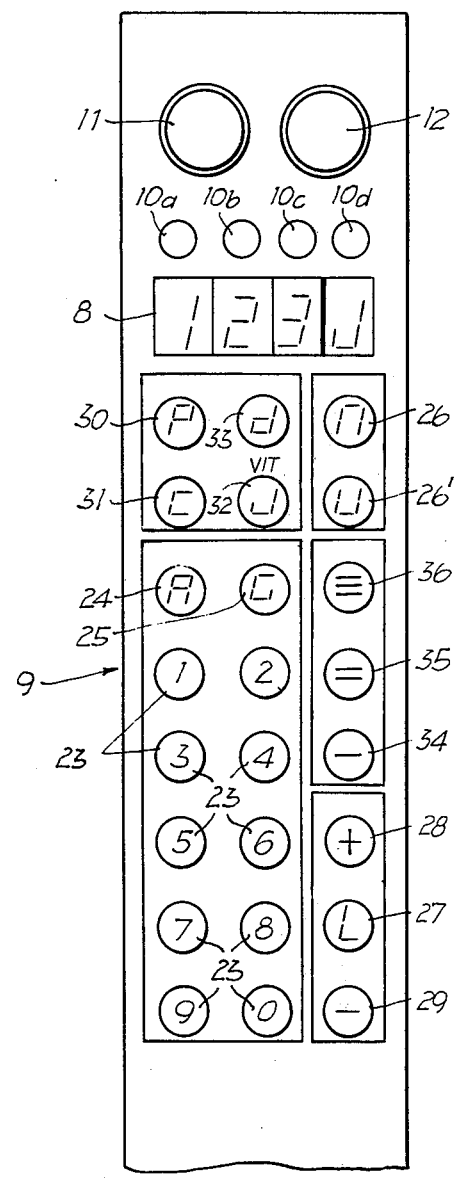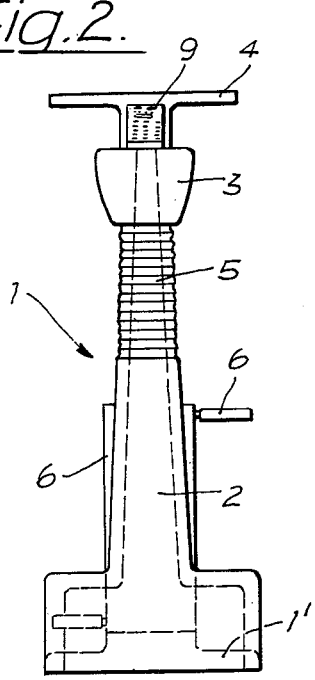

ERGOMETER

BACKGROUND OF THE INVENTION

This invention relates to the physical exercise arts, and more particularly to an ergometer equipped with a device for determining and indicating at least one of the values that are significant when the ergometer is used.

Ergometers are known in which the speed of the user or exercisor is detemined and indicated when using the momentary speed of his movements. However, this value is unsuitable for determining the capacity applied by the user and the capacity of his circulation, at least when the propulsive output of the ergometer at least in a certain range is independent of the propulsive speed, which is the case in a number of known ergometers. A better ergometer is therefore a known ergometer in which by means of a receiver, a sequence of impulses corresponding to the pulse frequency and a tension which is proportional to the impulse frequency is produced which is indicated by means of a tension indicator. However, for the determination and indication of other significant values, the device of this known ergometer is not suitable. In addition, the accuracy and the manner of taking the mean is not satisfactory in all cases.

SUMMARY OF THE INVENTION

It is, therefore, a primary object of the invention to provide an ergometer which makes it possible to determine and indicate with sufficient accuracy all values that are significant when the ergometer is used. This is accomplished, according to the invention, by equipping the ergometer with an arithmetic computer with digital display.

By means of such a computer, technical values, such as the capacity to be applied by the user to operate the ergometer, as well as physiological values, such as the oxygen absorption capacity of the user per kilogram of body weight and minute, can be determined and indicated with sufficient accuracy. In addition, the stress device of the ergometer can be controlled by means of the computer in order to be able to carry out indicated stress or training programs.

The input of personal data of the user into the computer is necessary, especially for the determination of the physiological quantities. In a preferred method of construction, the computer is therefore equipped with an input unit with a keyboard as well as a stored program. After the input of the values required for the computations, the computer can then, by means of the stored programs, determine and indicate the desired values.

Since the heart-pulse frequency is a significant quantity for determining the stress of the user and the capacity of his circulation, and since, in addition, the heart-pulse frequency is required for determining a number of physiological quantities, a heart-pulse receiver is connected to the input unit in the case of the preferred construction.

The informational value of the propulsive output which the user applies to the ergometer is, at least for laymen, relatively unimportant. According to a preferred embodiment of the invention, the computer therefore determines the energy used by the user, i.e., the sum of the energy received by the ergometer and the energy used up by the efficiency of the human organism in the organism itself. This energy may, for example, be indicated as calories.

Since a training effect, namely a stress which promotes the efficiency of the organism of the user and especially his circulation, presupposes that the pulse frequency is increased for a certain time to an ideal value which depends on the personal data of the individual, for example, the age of the user, one may, by means of the device, determine the time during which the user has an ideal pulse frequency determined on the basis of the age of the user fed in by the keyboard. However, the quantity of the training supplies more precise information on the training effect. In the case of the preferred embodiment, the time of the training and the intensity of the training are therefore determined and used as basis for determining the quantity of the training. The quantity of the training then shows how long the use of the ergometer must be continued in order to obtain a desired training effect.

Since the measurement of the heart-pulse frequency of a moving person presents certain difficulties because of disturbances of the contact between the person and the receiver, it is advantageous to also determine the heart-pulse frequency by means of the computer.

The decisive value for determining the circulatory capacity of a human being is the oxygen absorption capacity per kilogram body weight and minute. The maximum stress capacity or capacity of the circulation corresponds to the highest possible aerobic transformation of energy within the human body which again is proportional to the volume of the maximum oxygen absorption per time unit.

The computer of the ergometer according to the invention makes it possible to determine this data on the basis of the values fed in by means of the input device in regard to age, sex, weight, pulse frequency and performance output of the user as well as the stored mathmematical formulas. For reasons of comparison, all values are expressed in a sex, age and weight specific manner. By means of a correction factor which takes into consideration the age and the weight of the user, one can therefore, by means of the computer, determine a value which is a measurement of the fitness of the user.

With the above and other objects in view that may become hereinafter apparent, the nature of the invention may be more clearly understood by reference to the several views illustrated in the attached drawings, the following detailed description thereof, and the appended claimed subject matter, wherein:

FIG. 1 is an elevated view of an ergometer constructed in accordance with this invention;

FIG. 2 is a rear elevation view of the ergometer illustrated in FIG. 1;

FIG. 3 is an enlarged fragmentary plan view of the input unit and indicating display of the ergometer of this invention.

DETAILED DESCRIPTION OF PREFERRED EMBODIMENT

Figure 4:
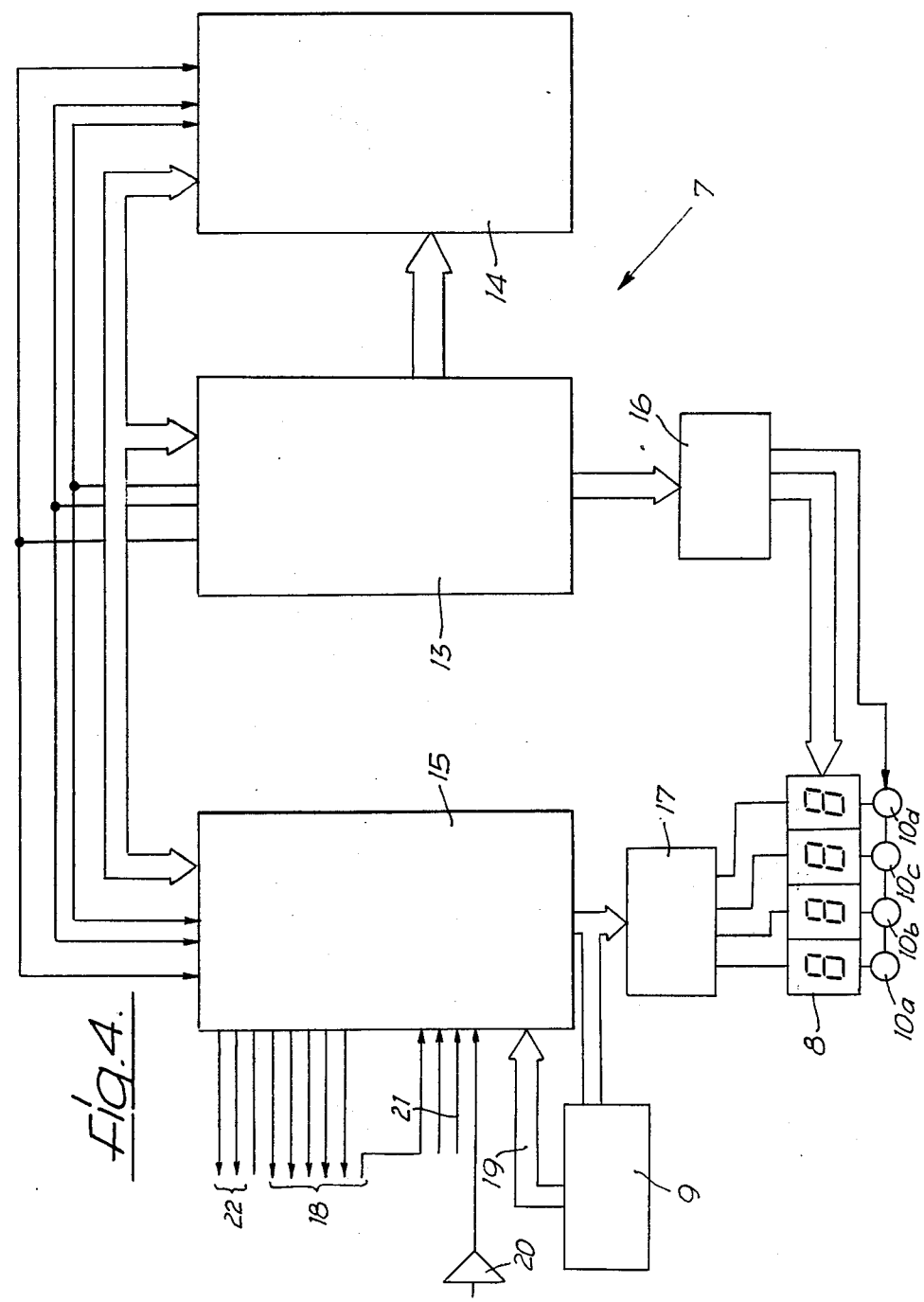
FIG. 4 is a block schematic diagram of the computer and connected devices of this invention.

Referring now to the drawings in detail, there is illustrated in FIG. 1 an ergometer generally designated by the numeral 1. The ergometer 1 includes a housing 2 which stands on a base plate 1'. On the upper side of the housing 2 there is a seat 3 as well as a detachable hand grip 4 for the user. The upper part of the housing 2 which carries the seat 3 and the hand grip 4 is developed in such a way that it is vertically adjustable in relation to the lower part. A bellows device 5 balances the varying distances between the upper and the lower part of the housing 2.

A foot pedal 6 is located in the lower part of the housing 2, which the user rotates with his feet. Over a gear unit, which is not shown, and which may, for example be a V-belt gear, a direct-current generator, which is also not shown, is coupled with a foot pedal 6. This direct-current generator, in the illustrated embodiment, has permanent magnets for generating the exciter field. A ventilator is also gear-connected with the foot pedal 6, the air current of which cools the components that become hot.

An electronic load control is connected to the output terminals of the generator which forms an adjustable load device. In order to keep the load current at an indicated nominal value and in the case of changes of the nominal value, to change the load current respectively, the load control is equipped with a PI-regulator. The nominal value for the capacity received by the load device is changeable, in the preferred embodiment in 26 phases of 10 watts each.

In addition to the electronic circuit for the control or regulation of the load control unit, an electronic device is installed into the housing 2, which has an arithmetic computer, referred to generally in FIG. 4 by the numeral 7, with which a four-digit digital indicator device 8 as well as an input unit 9 are connected. The latter, as well as the indicator device 8, additional indicator lamps 10 to 10d, and two connector sockets 11 and 12, are located in a recess of the upper side of the housing 2 near the hand grip 4, and thus within view of the user.

As seen in FIG. 4, the computer 7 has a central unit 13, a stored program 14 and an input-output block 15 with which it is connected over the necessary wirings. The central unit 13 and the input-output block 15, over intensifiers 16 and 17, control the indicator device 8 and the additional indicator lamps 10a to 10d. As shown by FIG. 4, the input-output block 15 is also, over wirings 18, connected with the control device for the load control unit as well as over the wirings 19 connected with the input unit 9. Another connection is planned for a heart impulse signal amplifier 20. In addition, the input-output block 15 has a connection 21 for the selection of varying methods of operation as well as connecting points 22 for the connection of a remote control.

As seen in FIG. 3, the input unit 9 contains keys 23 for the numbers 0 to 9 for the input of numerical values. By means of the keys 23 and a key 24, the age of the user can be fed into the computer 7. The input of the weight of the user is carried out in connection with key 25. By means of the keys 26 and 26', the fact whether the user is of male or female sex is fed into the computer. The activation of a key 27 results in an indication by the indicator device 8 of the capacity that has to be applied to operate the ergometer. The activation of a key 28 has the effect that the necessary propulsive output is adjusted by always one additional phase. Correspondingly the activation of a key 29 results in a gradual decrease of the propulsive power. By means of the activation of a key 30, the mean heart pulse frequency, by means of the activation 31, the energy which the user has expended since he started using the ergometer, taking into account the efficiency of the organism, is indicated by the indicator device in calories. If the user activates a key 32, the indicator device 8 will indicate that period of time which, while the ergometer was used, the heart-pulse frequency was in the ideal range which has been determined previously. The activation of a key 33 results in the fact that the indicator device 8 indicates a value which constitutes a measurement for the fitness of the user. This value is determined on the basis of the oxygen absorption capacity of the user per kilogram body weight and minute taking into account the heart-pulse frequency, the age, the weight and the sex. Finally, the input unit 9 also has three keys 34, 35 and 36, by the operation or activation of which various training (exercise) phases may be selected. In the illustrated embodiment, key 34 is assigned the training (exercise) phase "start", the key 35 is assigned the training (exercise) phase "normal" and key is assigned the training (exercise) phase "sport". In the case of these various training (exercise) phases, varying values of the ideal heart-pulse frequency are used as a basis for the determinations. In the case of the phase "start", the ideal heart frequency is determined according to formula 165 minus age, in the case of the phase "normal", according to formula 175 minus age, and in the case of phase "sport", according to formula 185 minus age.

All of the keys have an appropriate symbol, in order to facilitate the operation. This symbol appears in the last digit of the indicator device 8, when it indicates the corresponding value.

The energy supply is carried out by means of the direct-current generator as soon as it has reached the minimum rotational speed for the generation of a tension of the amount of the operating voltage and by means of a rechargeable boosting battery which is connected to the direct-current generator.

The ergometer is turned on and off over two contacts of a five-pole plug which is inserted into the plug socket 11. The plug is an attaching plug of the heart-pulse frequency receiver. This has electrodes (not shown) over which the heart muscle currents, as in the case of the electrocardiogram, are led off. Filters as well as the amplifier 20 are connected at the outlet side of the electrodes. Rectangular impulses are therefore led to the input-output block 15, the period duration E of which corresponds to the heart pulse period.

When the electrodes are properly placed, the clear indicator lamp 10a with the heart-pulse frequency will flash after the insertion of the plug into the plug socket 11. The symbol A also flashes in the last digit of the indicator device 8 in order to remind the user that he must now feed in the numerical value for his age by means of the keys 23. The fed-in numerical value is indicated by the indicator device 8 together with the appropriate symbol. By pressing the key 24, the value is transferred to the stored program 14 and the digital display is cancelled. Then the symbol G flashes on the indicator device 8, and the numerical value of the weight must now be fed in by the user in the same way.

Subsequently, the symbols for the "start, normal and sport" exercise phases will, in an alternating manner, light up in this sequence long enough for the user to press one of the keys and thus feed the selected exercise phase into the stored program.

Now, the symbols for male or female sex will light up in an alternating manner, so that the user will indicate his sex by pressing key 26 or 26'.

Then symbol L will flash for the propulsive power. The nominal value is first adjusted to a certain value. If the user activates key 28, the nominal value is increased. The activation of key 29 results in a decrease of the nominal value. The selected power or capacity is shown by the indicator device 8 until the key 27 is pressed, in which case the flashing of the symbol is also terminated.

All indicated values may be changed at all times by activating the appropriate key.

When all above-mentioned values are fed in, the number zero will appear in the third digit of the indicator device 8, and in the last digit, the symbol ⌐⌐ will appear for the training or exercise quantity. The unit of measure for the training (exercise) quantity is "vit min", since the training (exercise) quantity corresponds to the product of the training (exercise) intensity (unit of measure "vit") and the time of training (exercise) (unit of measure "min"). The significance of the quantity of training or exercise lies in the fact that the obtainable specific circulatory capacity increases with the average training (exercise) quantity per day which is the reason for being able to determine the effect of the exercise of a certain training or exercise quantity.

The intensity of training is the specific capacity of training or exercise, thus the respective physical performance per kilogram body weight above a threshold value. A training (exercise) effect is namely obtained only if the intensity of training is above a threshold value.

The flashing of the symbol ⌐⌐ in the indicator device 8 means that henceforth the quantity of training (exercise) is calculated and can be indicated. The calculation takes place according to the formula intensity of training (vit) = $K_1 (L/G - K_2)$ Watts/kg.

In this formula
$K_1$ is a constant,
$K_2$ is the threshold value of the intensity of training in watts/kg,
$L_{ph}$ is the physical performance in watts,
$G$ is the body weight in kilogram.

By multiplication with the time of training $t$ in min, the quantity of training is obtained:

$$\sqcup \text{ (vit min)} = K_1 (\frac{L}{G} - K_2) \cdot t \; \frac{\text{Watts min}}{\text{kg}}$$

One may start from the fact that 100 vit min daily are sufficient to reach and maintain a good physical fitness.

As soon as the rotational speed of the direct-current generator is in the planned and permissible speed range, one of the indicator lamps 10b, 10c or 10d will flash. The yellow indicator lamp 10d will flash, when the mean heart-pulse frequency of the user is below an ideal value, namely $P < D - A$. The green lamp c will flash when the mean heart-pulse frequency is in the ideal range, and thus fulfills the requirement $(D - A) < P < (D - A + 15)$.

The red indicator lamp signals a heart-pulse frequency which is too high, since it is assigned to the condition $P > (D - A + 15)$.

In this case,
P is the mean heart-pulse frequency,
D is the value of the performance phase, thus 165, 175 or 185 and
A is the age of the user in years.

The calculation of the mean value of the heart-pulse frequency by means of the computer 7 is carried out according to the formula $$P = \frac{75000}{\sum_{E=0}^{E=25} i}$$

$i$ is here the number of the counting pulses which in the illustrated embodiment have a frequency of 50 Hz. E is the duration of the heart-pulse period. In the illustrated embodiment, the calculation of the value P is based on the number of the counting pulses, which fall into the time period of 25 heart pulse periods. The calculation of this number of counting pulses i takes place according to the formula $$\sum_{E=0}^{E=25} i = \sum_{E=i}^{E=24} i - \frac{\sum_{E=-1}^{E=24} i}{25} + \sum_{E=24}^{E=25} i$$

This manner of calculation has the advantage that only two storage spaces are required. In order to eliminate interfering influences, the value P may only change by one unit upwards or downwards in each pulse period E. In addition, those heart-pulse periods are not taken into account which are outside the range between 0,2 seconds and 2 seconds.

Two counters store the value of the training (exercise) quantity or the number of the calories used by the user, in which case the calculation of the last mentioned value takes place according to the equation $$C = K_3 \cdot \sum_{t=0}^{t_1} L \cdot t$$

in cal. In the equation
$K_3$ is a constant,
L is the propulsive output applied by the user in watts,
$t$ is the time in minutes.

The values of the training quantity in vit min. of the used calories in cal and the heart-pulse frequency in 1/min may be indicated selectively on the indicator device 8 by pressing the keys 31, 32 or 30, in which case the appropriate symbol is indicated simultaneously.

If the feeding of the apparatus by the generator does not take place, the digital display on the indicator device 8 is extinguished after about 70 seconds. The counter for the training quantity is adjusted to zero. The other values will be maintained. The same will happen if the yellow indicator lamp 10d lights up or flashes for longer than about 70 seconds.

If a training (exercise) quantity of 90 vit min has been reached, the digital display will flash with a frequency of about 2 Hz., in order to draw the user's attention to the immediately imminent measuring moment. For, as soon as ⌐⌐ = 100 vit min is reached, the specific circulatory capacity or performance is calculated by the computer and indicated with symbol ⌐⌐ on the indicator device 8.

The maximum stress capacity of the circulation or the circulatory capacity corresponds to the highest possible aerobic transformation of energy in the human body, which again is proportional to the volume of the maximum oxygen absorption per time unit. For these values, the following formulas will apply:

$$O_2 \max (\frac{\text{ltr}}{\text{min}}) = \frac{1}{t} \cdot f(P, Lph)$$

-continued $$E\ \max\ (\frac{cal}{min}) = K_4 \cdot \frac{1}{t}\ O_2\max = K_5 \cdot \frac{1}{t} \cdot f(P,Lph)$$

$$L\ \max\ (Watt) = K_6 \cdot \frac{1}{t}\ E\max = K_4 \cdot K_5 \cdot \frac{1}{t}\ O_2\max = \frac{K_4 K_5}{t}\ f(P,Lph)$$

$$d_{vit} = K_6 \cdot L_{max} \cdot \frac{1}{G} \cdot f(A) \cdot f(S) = K_7 \cdot \frac{1}{G \cdot t}\ f(A)f(S)f(P,Lph)$$

In this case,
$O_{2max}$ = oxygen absorption per minute with maximum circulatory stress
$E_{max}$ = energy transformation per minute with maximum circulatory stress
$L_{max}$ = maximum circulatory capacity,
$d_{vit}$ = specific circulatory capacity,
$K_7 = K_4 \cdot K_5 \cdot K_6$ = constant,
G = body weight
t = time,
A = age,
S = sex,
P = heart-pulse frequency,
$L_{ph}$ = physical performance or capacity Because of the sex, age-and weight-specific data concerning the circultory capacity, this may also be called the measurement for physical fitness.

The unit of measure for the circulatory capacity determined by the computer which may also be called maximum stress capacity or capacity of the circulation taking into account the sex, age and weight, is "DYNA-VIT".

In the preferred embodiment, the specific circulatory capacity $d_{vit}$ for male users is calculated according to the formula $$H_1 = S_m \cdot \frac{1}{K_1 - K_2(A + K_3)}$$

and for female users according to the formula $$H_2 = S_w \cdot \frac{1}{K_4 + \frac{A - K_5}{K_6 - K_7}}$$

in which $S_m$ is the maximum oxygen absorption capacity per kilogram body weight and minute for male persons, $S_w$ is the corresponding value for female persons,
A is the age in years and
$k_1$ to $k_7$ are constants.

The maximum oxygen absorption capacity per kilogram body weight and minute for male users is calculated to the formula $$S_m = \frac{M(k_8 P + k_9)}{P - k_{10}} \cdot (k_{11}L^2 + k_{12}L + k_{13})$$

for female users according to the formula $$S_w = \frac{M(k_{14}P + k_{15})}{P - k_{16}} \cdot (k_{17}L + k_{18})$$

in which case $$M = \frac{K_{19} \cdot A + k_{20}}{K_{21}A + k_{22}} \cdot \frac{1000}{\text{weight (kg)}}$$

and $k_8$ to $k_{22}$ are constants.

In the meantime, the two counters for the number of calories and the size of the training quantity continue to count. The level of the counter can subsequently be indicated again by activating the corresponding keys. After reaching the value ⌊ ⌋ = 100 vit min, the pertaining counter is no longer cancelled if the indicator lamp 10d lights up or flashes longer than approximately 70 seconds.

During the pressing of the keys 24, 25, 27, 30 or 33, the corresponding stored values and their symbols are indicated by the indicator device 8. Subsequently, the training quantity with the symbol ⌊ ⌋, the number of the used calories C or the pulse frequency P will appear again.

By pulling the plug of the heart-pulse frequency receiver, the ergometer and the battery are turned off. All other displays are distinguished.

If the ergometer is to be operated without connected electrodes of the heart-pulse frequency receiver, only the number of the calories used up by the user and the training (exercise) quantity are determined.

Although only a preferred embodiment of the invention has been specifically illustrated and described herein, it is to be understood that minor modifications could be made therein without departing from the spirit of the invention.

I claim:

1. An ergometer for measuring and indicating physical exercise parameters comprising a housing including means for a user to apply physical energy into the ergometer, a digital computer disposed in said housing having digital display means arranged for ready observation by the user for determining and indicating at least one of said exercise parameters during the application of physical energy by the user, said computer including a memory for storing said exercise parameters and at least one program, input unit means for providing said computer with values corresponding to personal data regarding the user, and means for the user to selectively summon from said computer during use information corresponding to said exercise parameters for display on said digital display means.

2. An ergometer as defined in claim 1, further including a heart-pulse receiver adapted to be operatively connected to the user for measuring the heart-pulse frequency of the user, and means for connecting said heart-pulse receiver to said input unit means.

3. An ergometer as defined in claim 2, wherein said input unit means includes means for providing said computer with values corresponding to the age of the user, and wherein said computer includes means for determining and indicating when the measured heart-pulse frequency of the user, based on the provided age values, reaches a predetermined ideal frequency.

4. Ergometer as defined in claim 2, wherein said computer includes means for determining and indicating a sliding mean value of the measured heart-pulse frequency of the user.

5. Ergometer as defined in claim 4, wherein said input unit means includes means for providing said computer with values corresponding to the age, sex and weight of the user, and wherein said computer includes means for determining and indicating physiological values as a function of said provided values, the means value of the measured heart-pulse frequency and the energy expended by the user.

6. Ergometer as defined in claim 5, wherein said computer includes means for detemining and indicating the maximum oxygen absorption capacity of the user per kilogram body weight and minute.

7. An ergometer as defined in claim 1, wherein the exercise parameters determined and indicated by said computer include energy expended by the user.

8. An ergometer for measuring and indicting physical exercise parameters comprising a housing including means for a user to apply physical energy into the ergometer, an arithmetic computer disposed in said housing having digital display means for determining and indicating at least one of said exercise parameters during the application of physical energy by the user, said computer including a memory for storing said exercise parameters and at least one program, input unit means for providing said computer with values corresponding to personal data regarding the user, said input unit means including means for providing said computer with values corresponding to the body weight of the user and said computer includes means for measuring the elapsed exercise time during which physical energy is applied by the user, means for determining and indicating exercise intensity as a function of the energy expended and the body weight of the user, and means for determining and indicating exercise quantity as a function of the elapsed exercise time.

9. An ergometer for measuring and indicating physical exercise parameters comprising a housing including means for a user to apply physical energy into the ergometer, a digital computer disposed in said housing for determining and indicating at least one of said exercise parameters during application of physical energy by the user, digital display means positioned in said housing and arranged for ready observation by the user, said computer having a memory for storing said exercise parameters and at least one program, input unit means for providing said computer with values corresponding to the age, sex, weight and heart-pulse frequency of the user during the application of physical energy by the user, said computer including means for determining and calculating the specific circulatory capacity of the user as a function of said provided values and the amount of energy expended by the user, and means for the user to selectively summon from said computer during use information corresponding to said exercise parameters for display on said digital display means.

* * * * *